United States Patent [19]

Ting et al.

[11] 4,454,043
[45] Jun. 12, 1984

[54] COLUMN SWITCHING PROCEDURE

[75] Inventors: Chihyuan C. Ting, Creve Coeur, Mo.; David F. Tomkins, Muscatine, Iowa; Melvin L. Rueppel, Kirkwood, Mo.

[73] Assignee: Monsanto Company, St. Louis, Mo.

[21] Appl. No.: 207,539

[22] Filed: Nov. 17, 1980

[51] Int. Cl.[3] .............................................. B01D 15/08
[52] U.S. Cl. .................................. 210/659; 210/198.2
[58] Field of Search ...................... 210/656, 659, 198.2

[56] References Cited

U.S. PATENT DOCUMENTS

| | | | |
|---|---|---|---|
| 3,686,117 | 8/1972 | Lauer et al. | 210/659 |
| 3,700,695 | 12/1972 | Rueppel | 260/534 R |
| 3,950,402 | 4/1976 | Franz | 260/502.5 |
| 3,954,848 | 5/1976 | Franz | 260/502.5 |
| 3,966,596 | 6/1976 | Stevens et al. | 210/198.2 |
| 3,969,398 | 7/1976 | Heashman | 260/502.5 |
| 3,977,860 | 8/1976 | Franz | 71/86 |
| 4,070,284 | 1/1978 | Fujita et al. | 210/198.2 |
| 4,073,725 | 2/1978 | Takeuchi | 210/659 |

OTHER PUBLICATIONS

Introduction to Modern Liquid Chromatography by Snyder and Kirkland, 2nd Edition, John Wiley & Sons, New York, 1979.

Primary Examiner—John Adee
Attorney, Agent, or Firm—Gordon F. Sieckmann; Charles E. Krukiel

[57] ABSTRACT

A method for increasing the capacity of a chromatographic system useful for the quantitative determination of at least one component of interest at a trace level concentration in a multi-component composition.

17 Claims, 1 Drawing Figure

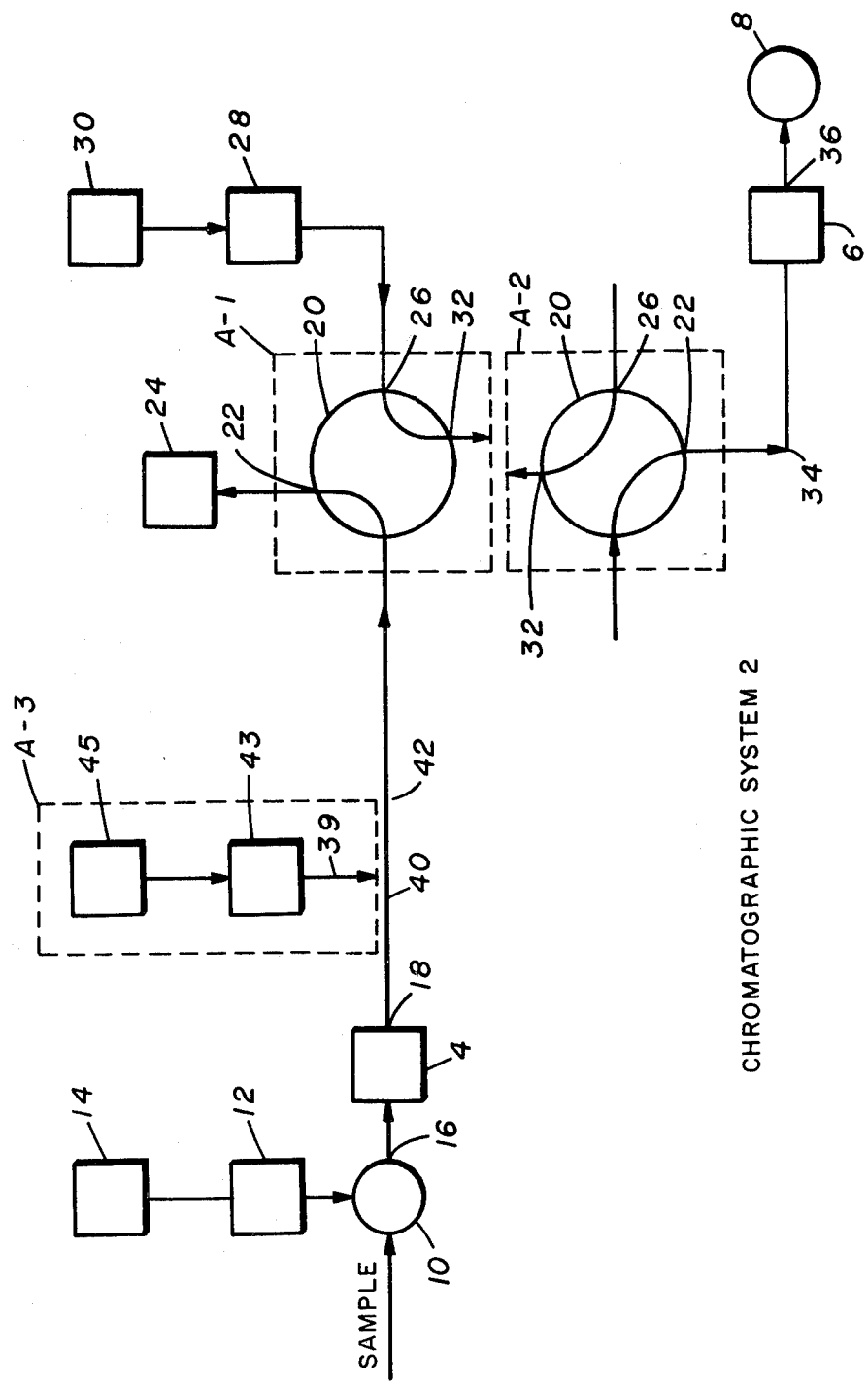

COLUMN SWITCHING PROCEDURE

The present invention relates to a chromatographic method and apparatus having an improved capacity. More particularly, this invention relates to a chromatographic method and apparatus having an improved capacity and useful for determining the concentration of compounds at race level concentrations in a multi-component composition. Most particularly, this invention relates to a chromatographic method and apparatus having a high column loading capacity useful for determining the trace level concentrations of glyphosates or polar alkyl nitrosoamines at trace level concentrations in aqueous solutions thereof.

The term "trace level" is employed throughout the claims and description to mean a concentration of a component of interest in the range from about 1 to about 1000 and preferably from about 5 to about 100 parts per billion by weight or volume.

The last few years have brought an increased environmental awareness coincident with a need to monitor process streams as well as effluent streams of the chemical process industries in order to determine the composition of streams containing components such as the aforementioned and others.

These needs have evoked a corresponding need in the trace level organic analysis area. Such need in the trace level organic analysis area has mandated the use of sohpisticated HPLC chromatographic methods and apparatus. In those situations where sophisticated HPLC chromatographic equipment has been employed, the tremendous ability of HPLC to separate and analyze complex organic mixtures is now widely appreciated as never before.

Various techniques are known in the art which relate to the use of chromatographic techniques for determining trace organic analysis. These techniques include quantitative and qualitative analysis by HPLC, preparative scale separations, gradient elution and column switching, sample pre-treatment and reaction detectors, automatic systems for higher volume testing and/or samples requiring pretreatment, troubleshooting and sample antifacts such as band tailing. The aforementioned and other chromatographic techniques are described in detail in "Introduction to Modern Liquid Chromatography", L. R. Snyder and J. J. Kirkland, John Wylie & Sons, Inc., 2nd Edition, July, 1979.

Some chromatographic systems employ multiple stages to separate multi-component compositions. Such systems use two or more chromatographic columns arranged in series. These systems typically employ a switching valve mechanism equipped with a time or equivalent arrangement between two or more chromatographic columns to select one or more adjacent bands from a first chromatographic column eluate as feed to a second chromatographic column and thereafter as feed to a coupled reaction detector system.

In spite of the aforementioned and other chromatographic methods and apparatus, there is still a need at the present time for an improved chromatographic method and apparatus which offers a high capacity coupled with a high sensitivity for trace level organic analysis of multi-component compositions.

OBJECTS

It is a primary object of this invention to provide an improved chromatographic method and apparatus having a high capacity coupled with a high sensitivity to trace level components.

It is an additional object of this invention to provide an improved chromatographic method and apparatus for the trace organic determination of polar alkyl nitrosoamines and glyphosate compounds in a multi-component composition.

It is another object of this invention to provide a chromatographic system having a high column linear capacity coupled with a maximum sensitivity for the trace organic determination of polar alkyl nitrosoamines and glyphosates in a multi-component composition.

BRIEF DESCRIPTION OF THE INVENTION

The foregoing and other objects of the invention are accomplished in a method of increasing the capacity of a chromatographic system useful for the quantitative determination of at least one component of interest in a multi-component composition at trace level concentrations.

This method comprises admixing a portion of a multi-component composition with a first mobile phase carrier to form a chromatographically separable composition. The chromatographically separable composition is passed into a first chromatographic separation zone having as packing therein ion exchange resins having an average particle diameter in the range from about 30 to about 1000 microns. An eluent is thereby formed of each individual component of the multi-component composition.

The eluent of the component of interest is retained within the chromatographic system and is passed into a second chromatographic separation zone serially connected to an outlet of the first chromatographic separation zone. The second chromatographic separation zone has a packing therein ion exchange resin having an average particle diameter in the range from about 3 to about 15 microns. A second mobile phase carrier is passed into the second chromatographic separation zone thereby forming a purified eluent containing the component of interest in a concentrated form.

The purified eluent is thereafter passed into an analytical detection system serially connected to the outlet of the second chromatographic separation zone whereby the concentration of the component of interest is determined. The concentration of the component of interest in the multi-component composition is determined from the concentration of interest in the purified eluent.

DETAILED DESCRIPTION OF THE DRAWINGS

For a better understanding of the principles and function of the invention, the same will now be described by way of illustrative example with reference to a drawing in which the FIGURE is a schematic block diagram of a preferred chromatographic system employing therein the process of this invention.

DETAILED DESCRIPTION OF THE INVENTION

The present invention is particularly applicable for use in a chromatographic system employing a column switching technique for determining trace organic analysis.

The FIGURE depicts chromatographic system 2 of applicants' invention comprising first chromatographic separation zone 4 having packing therein (not shown)

serially connected to an inlet of second chromatographic separation zone 6 having packing therein (not shown) the outlet of which is serially connected to an inlet of analytical detection system 8 with process connections therebetween as more particularly described hereafter.

Sample injection port 10 is connected with the output of transfer pump 12 employed to supply a first mobile phase carrier (not shown) from a first mobile phase carrier storage 14 to sample injection port 10. Outlet 16 of sample injection port 10 is connected to first chromatographic separation zone 4. Outlet 18 of first chromatographic separation zone 4 is thereafter connected to multi-position transfer system 20.

The FIGURE shows two embodiments A-1 and A-2 of alternate process connections of multi-position process system 20.

With respect to embodiment A-1, outlet 22 of multi-position transfer system 20 is connected to intermediate storage zone 24. Inlet process connection 26 of multi-position transfer system 20 is connected to transfer pump 28 which is employed to transfer a second mobile phase carrier (not shown) from second mobile phase carrier storage 30 to multi-position transfer system 20. Outlet 32 of multi-position diverter system 20 is connected to inlet 34 of second chromatographic separation zone 6. Outlet 36 of second chromatographic separation zone 6 is connected to analytical detector system 8.

In a second position shown in A-2, outlet process connection 22 of multi-position transfer system 20 is connected to inlet 34 of second chromatographic separation zone 6 and outlet 32 of multi-position diverter system 20 is connected to intermediate storage zone 24 for subsequent processing or disposal.

Multi-position transfer system 20 comprises a control system (not shown) further comprising an analytical detection system associated with first chromatographic separation zone 4 having means (not shown) for generating and transmitting a process signal (not shown) associated with the admission of a sample of a multi-component composition of interest to first chromatographic separation zone 4, an actuator (not shown) capable of selecting positions of a multi-position diverter valve (not shown) thereof upon receipt of a process directive signal (not shown), and a process system controller (not shown) having means (not shown) for generating and transmitting to the actuator (not shown) a process directive signal (not shown) upon receipt of a process signal and manually entered external signals (not shown).

Means (not shown) for generating and transmitting the process directive signal comprises means for receiving the process signal from the analytical system, means for a receipt of and storage of external signals, means for comparing process signals and external signals and generating differences therebetween and means for generating and transmitting to an actuator a process directive signal porportional to the differences. Typically, the multi-position transfer system comprises a six port multiposition valve, the actuator comprises a pneumatic valve positioner, and the process controller comprises a programmable sequencer or a microprocessor. Signal transmitting, generating, storing and handling means are provided by electrical switches, relays, wiring and the like readily apparent to those skilled in the art.

The aforementioned chromatographic method and apparatus can be effectively utilized to provide an increased capacity in the trace level analysis of a multi-component composition. The term "multi-component composition" is employed throughout the claims and description to mean a composition containing more than one component and includes compositions such as mixtures as well as true solutions.

The portion of the multi-component mixture selected for use with the process of this invention is typically a sample size having a volume in the range from about 0.01 to about 5 and preferably from about 1 to about 2 milliliters although greater or lesser sample sizes may be employed.

The term "chromatographic separation zone" is employed throughout the claims and description to mean any zone capable of effecting a separation of the components of a multi-component composition and includes chromatographic zones such as columns of any shape, size, description or composition.

The term "packing" is employed throughout the claims and description to include any ion exchange resin or any material employed in the internal volume of a chromatographic separation zone and capable of retaining thereon a component of interest releasable upon elution with an appropriately selected mobile phase carrier. The packing employed in the first chromatographic separation zone in a first embodiment of this invention has a particle size diameter in the range from about 30 to about 1000 and preferably from about 35 to about 400 microns. Without being bound by theory, it is believed that use of the aforedescribed size of packing enhances the capacity of the first chromatographic separation zone.

The type of packing which may be employed in the first chromatographic separation zone and the second chromatographic separation zone is selected by those skilled in the art to retain a component of interest within a discreet zone of the packing which is releasable upon elution with an appropriately selected mobile phase carrier. Typical packing includes polystyrene divinyl benzene resin and silica base packing.

Illustrative polystyrene divinyl benzene resin includes anion, cation and reverse phase forms.

Typical anion forms of polystyrene divinyl benzene resin include those resins selected from the group consisting of hydroxide, formate, acetate, chloride, bicarbonate, sulfite, sulfate, nitrite, nitrate, phosphate, bromide, iodide, fluoride, carboxylate, mixtures thereof and the like.

Illustrative silica base packing includes anion, cation, normal and reverse phase.

The term "mobile phase carrier" is employed throughout the claims and description to include any composition capable of being passed into a chromatographic separation zone to effect the elution of a compound temporarily retained in the packing of the chromatographic separation zone.

The particular mobile phase carrier associated with first chromatographic separation zone 4 is selected to correspond with the type of packing employed in first chromatographic separation zone 4.

For example when a cation form of ion exchange resin is employed as packing in a first chromatographic separation zone, a typical mobile phase carrier comprises an aqueous solution of an inorganic salt and an organic solvent such as is more particularly described hereinafter with respect to use as a second mobile phase carrier.

When an anion type ion exchange resin is employed as packing in first chromatographic separation zone 4, typically a first mobile phase carrier comprises an aqueous solution of a hydrogen halide, an aqueous solution of an alkali metal halide, mixtures thereof and the like.

Illustrative hydrogen halides include hydrogen chloride, hydrogen iodide, hydrogen fluoride, hydrogen bromide and mixtures thereof.

Illustrative alkali metal halides include sodium chloride, sodium iodide, sodium fluoride, sodium bromide, potassium chloride, potassium iodide, potassium bromide, potassium fluoride, lithium chloride, lithium iodide, lithium bromide, lithium fluoride and mixtures thereof.

However, an aqueous solution of sodium chloride is preferred as a first mobile phase carrier when an anion type ion exchange resin is employed as packing in a first chromatographic separation zone.

The concentration of the hydrogen halide or alkali metal halide or mixture thereof employed as a salt in an aqueous solution as a first mobile phase carrier is in the range from about 0.001 to about 0.5 and preferably from about 0.2 to about 0.4 molar. Those skilled in the art will recognize that greater or lesser concentrations of hydrogen halide or alkali metal halide may be employed as a salt in the first mobile phase carrier.

When cation exchange resin is employed as the packing in the first chromatographic separation zone, it is preferred to employ water purified to a grade at least equivalent to high pressure liquid chromatography grade water as a first mobile phase carrier.

Typical materials of construction of the first chromatographic separation zone may be metallic or plastic but preferably are stainless steel.

The type of packing employed in the second chromatographic separation zone may be the same or different as the packing employed in the first chromatographic separation zone.

The second mobile phase carrier associated with the second chromatographic separation zone is typically an aqueous solution of an inorganic salt and an organic solvent.

Typical inorganic salts include salts such as potassium phosphate, monobasic; sodium phosphate, monobasic; and ammonium phosphate, monobasic, although potassium phosphate, monobasic is preferred. The concentration of inorganic salts is in the range from about 0.005 to about 0.5 and preferably from about 0.05 to about 0.4 molar although greater or lesser concentrations of inorganic salt may be employed.

Typical organic solvents include acetonitrile, pyridine, dimethylsulfoxide, cyclohexane, 2-propanol, 1-propanol, ethanol, isopropyl alcohol, methanol, butanol, mixtures thereof and the like, although methanol is a preferred organic solvent.

The eluant of the second chromatographic separation zone may be admixed with a reactant solution capable of reacting with the component of interest in said eluant of second chromatographic separation zone or in the analytical detector means to produce a derivative of the component of interest preferably an analytically detectable product, such as a colored complex.

Those skilled in the art will recognize that any convenient form of method of detection may be employed as analytical detection means 8. Suitable analytical detector systems include conventional detector and reaction detector systems such as those known in the art as the Griess reactor system or modified Griess Reactor System although any convenient reactor system may be employed. Other acceptable detector systems include thermal energy analyzer, electrochemical detector, photoionization detector, refractive index, chemiluminescence detector, spectrophotometer detector, fluorescence detector, infrared, mass spectrometer, nuclear refractive resonance, combinations thereof and the like.

In the practice of applicants's invention, a column switching technique may be suitably employed with the system shown in the FIGURE employing multi-position diverter system 20. A real time count $T_0$ is initiated with the admission of a sample of multi-component composition to the first chromatographic separation zone. A portion of the eluent from the first chromatographic separation zone is passed to the second chromatographic separation zone when $T_0$ exceeds a preselected time interval $T_1$ wherein $T_1$ is associative of the real time required for the beginning of elution of applicants' component of interest from the first chromatographic separation zone. Passing of the eluent from the first chromatographic separation zone to the second chromatographic separation zone is terminated when $T_0$ exceeds ($T_1$ plus a $\Delta T$) wherein $\Delta T$ is a real time interval associated with a maximum peak height on the chromatographic analysis (detector) for the component of interest. Thereafter for a time $T_2$, only second mobile phase carrier is passed to the second chromatographic separation zone. After $T_0$ exceeds ($T_1 + \Delta T + T_2$), the sample injection procedure is repeated and the time count is repeated.

Typical aqueous solutions of multi-component composition which may be analyzed by the method of this invention include any aqueous mixture containing glyphosate or any acidic type components of interest at trace level concentrations.

The term "glyphosate" is employed throughout the claims and description to mean N-phosphonomethylglycine, salts thereof, derivatives thereof as well as glyphosate-related compounds having glyphosate moiety structures

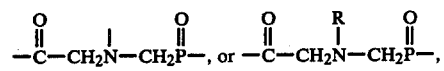

wherein R is

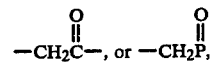

and including, but not limited to the following:
  monocyclohexylamine salt of N-phosphonomethylglycine;
  di(methylamine) salt of N-phosphonomethylglycine;
  di(dimethylamine) salt of N-phosphonomethylglycine;
  di(ethylamine) salt of N-phosphonomethylglycine;
  di(n-propylamine) salt of N-phosphonomethylglycine;
  di(morpholine) salt of N-phosphonomethylglycine;
  mono(stearlyamine) salt of N-phosphonomethylglycine;
  mono(tallowamine) salt of N-phosphonomethylglycine;
  mono(methylbutyl) salt of N-phosphonomethylglycine;
  mono(butylamine) salt of N-phosphonomethylglycine;
  n-dibutylamine salt of N-phosphonomethylglycine;

n-octadecylamine salt of N-phosphonomethylglycine;
methoxyethylamine salt of N-phosphonomethylglycine;
ethylenediamine salt of N-phosphonomethylglycine;
dipropanolamine salt of N-phosphonomethylglycine;
chloroethylamine salt of N-phosphonomethylglycine;
phenoxyethylamine salt of N-phosphonomethylglycine;
mono(triethylamine) salt of N-phosphonomethylglycine;
mono(diethylenetriamine) salt of N-phosphonomethylglycine;
monoisopropylamine salt of N-phosphonomethylglycine;
monomorpholine salt of N-phosphonomethylglycine;
monoaniline salt of N-phosphonomethylglycine;
monoethanolamine salt of N-phosphonomethylglycine;
monodiethanolamine salt of N-phosphonomethylglycine;
monoammonium salt of N-phosphonomethylglycine;
monosodium salt of N-phosphonomethylglycine;
disodium salt of N-phosphonomethylglycine;
trisodium salt of N-phosphonomethylglycine;
monopotassium salt of N-phosphonomethylglycine;
dipotassium salt of N-phosphonomethylglycine;
tripotassium salt of N-phosphonomethylglycine;
dilithium salt of N-phosphonomethylglycine;
monosodium salt of ethyl N-phosphonomethylglycinate;
monosodium salt of chloroethyl N-phosphonomethylglycinate;
methyl N-phosphonomethylglycinate;
dimethyl N-phosphonomethylglycinate;
ethyl N-phosphonomethylglycinate;
2-chloroethyl N-phosphonomethylglycinate;
n-propyl N-phosphonomethylglycinate;
and includes, but is not limited to, those glyphosate compounds, salts, esters and derivatives particularly described in U.S. Pat. Nos. 3,977,860 issued to John E. Franz on Aug. 31, 1976, 3,970,695 issued to Melvin L. Rueppel on July 20, 1976, 3,969,398 issued to Arnold Hershman on July 13, 1976, 3,954,848 issued to John E. Franz on May 4, 1976 and 3,950,402 issued to John E. Franz on Apr. 13, 1976. The teachings of the aforementioned patents are incorporated herein in their entirety by reference.

Acidic-type compounds which may be effectively analyzed by the method and apparatus of this invention comprise any acidic compounds including those having alkyl, phosphonic, aromatic, aryl or any functional group.

Typically for glyphosate the packing in the first chromatographic separation zone is any cation exchange resin of the aforedescribed size. Water or acidic-phosphate buffer is employed as a first mobile phase carrier. The packing in the second chromatographic separation zone is any strong anion ion exchange column and is of the aforedescribed size and type. Typically, a buffer solution of $KH_2PO_4$ is employed as the mobile phase carrier to the second chromatographic separation zone when glyphosate or an acidic type compound is the component of interest. This $KH_2PO_4$ buffer solution is typically prepared by dissolving $KH_2PO_4$ is methaol-water and adjusting the pH to about 2 to about 4 with acid. Normal HPLC degassing filtration procedures are followed.

If desired, a reactant solution may be admixed with the eluent of the second chromatographic separation zone containing the component of interest to form a derivative of the component of interest. When glyphosate is the component of interest, the reactant solution is a ninhydrin solution which comprises dimethylsulfoxide, deionized water, ninhydrin and lithium acetate buffer. Preparation of the ninhydrin solution is accomplished by admixing dimethylsulfoxide, deionized water, lithium acetate buffer (or sodium acetate buffer) and bubbling an inert gas through the composition for aeration. Ninhydrin is admixed with the aerated solution. In a separate container, hydrindantin is dissolved in dimethylsulfoxide with several milliliters of the aforedescribed ninhydrin solution and inert gas is bubbled therethrough.

A wetting agent is also employed comprising Brij 35 surfactant dissolved in deionized water and acidified. Without being bound by theory, it is believed that the use of the aforesaid ninhydrin solution as a reactant with glyphosate enables the production and subsequent detection of a derivative product species by colorimeter.

Portion A-3 of the FIGURE illustrates an embodiment of the applicants' invention suitable for the detection of polar alkyl nitrosoamines in aqueous solutions. In this embodiment as shown in the FIGURE, an additional mobile phase carrier 39 is admixed with eluate 40 of first chromatographic separation zone 4 by means of pump 43 from storage 45 to form diluted eluate 42. A portion of diluted eluate 42 is thereafter passed to second chromatographic separation zone via multi-position divertor system 20 as aforedescribed.

Without being bound by theory, it is believed that use of the additional mobile phase carrier 39 in this embodiment enhances loading of the component of interest in the packing at the top of the second chromatographic separation zone thereby increasing the sensitivity and minimizing extra column effects of the process of this invention.

Aqueous solutions containing trace level concentrations of polar-substituted alkyl nitrosoamines may be analyzed by employing the aforedescribed embodiment. Such polar alkyl substituted nitrosoamines include the N-nitroso N-phosphonomethylglycine (NNG) which may be found at trace levels in aqueous solutions. Principally, aqueous solutions containing NNG may be minimally formed under glyphosate process production conditions where isopropylamine, water and nitrite compounds are present.

Polar-substituted alkyl nitrosoamines typically are those nitrosoamines characterized as having an acid hydrogen. Illustrative of the polar-substituted alkyl nitrosoamines are compounds of the formula

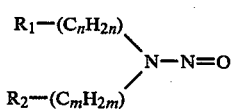

where n and m are independently integers from 1 to 6 and $R_1$ is a carboxy, phosphonic or sulphonic group and $R_2$ is a hydrogen or a group represented by $R_1$.

In this embodiment, packing material employed in the first chromatographic separation zone is typically a strong anion resin of the aforedescribed size while the packing employed in the second chromatographic separation zone is also a strong anion ion exchange resin of the aforedescribed size.

Typically, the first mobile phase carrier comprises an aqueous solution of an alkali metal halide, preferably, an aqueous solution of sodium chloride. The additional mobile phase carrier is water purified to a grade equivalent to HPLC water and is typically admixed with the eluent of the first chromatographic separation zone containing the N-nitrosoamine to form a diluted eluent, a portion of which is thereafter passed to the second chromatographic separation zone.

The second mobile phase carrier employed with this embodiment typically includes an aqueous solution of a potassium salt such as $K_2PO_4$ having an organic solvent typically methanol.

A reactant is generally admixed with the purified eluent of the second chromatographic separation zone and thereafter the reaction product is passed to a reaction detector for analysis. Generally, the purified eluent of the second chromatographic separation zone is admixed with a reactant composition comprising an aqueous solution of hydrobromic acid and hydrochloric acid which is believed to react with N-nitrosoamine to form a solution of nitrous acid, a derivative of N-nitrosoamine.

The nitrous acid solution is admixed and treated with a composition comprising sulfanilamide, hydrochloric acid and Brij 35 surfactant comprising a polyoxyethylene ether 23 lauryl alcohol as a wetting reagent which is believed to react with the nitrous acid to form a solution of a diazo intermediate. Thereafter, the diazo intermediate is reacted with N-1-naphthyl ethylenediamine hydrochloride to form a stable colored complex which is readily detectable using spectrophotometric means.

Those of skill in the art will recognize that the process of this invention may be employed to analyze compositions containing more than one trace level component as well as other major components whose concentration are greater by appropriate selection of mobile phase carrier and type of chromatographic packing.

The following examples are presented to define the invention more fully without any intention of being limited. All parts and percentages are by weight unless otherwise specified.

EXAMPLE 1

A sample of an aqueous solution containing glyphosate as a component of interest at trace level concentration was analyzed in accordance with the following procedure employing a chromatographic separation system similar to that shown in the FIGURE. The aqueous solution comprised a stock solution of 1000 ppm by weight and was prepared by dissolving 100 milligrams of 3X crystallized analytical grade glyphosate in 100 milliliters deionized water which was stored in a refrigerator until use. A series of working standards of 20, 40, 60, 80, 100 ppb was prepared by appropriate dilution of the stock solution.

The first chromatographic separation zone comprised a chromatographic column of AG50W-X8 (Bio-Rad) having as packing therein strong action cation exchange resin of 38 to 150 micron particle size. The second chromatographic separation zone comprised a DuPont Zorbax ® SAX 15 cm×4.6 mm column having as packing therein silica based anion ion exchange packing of phosphate form therein of 6 to 8 micron size.

A reactor and a detector system were serially connected to the outlet of the second chromatographic separation zone. The reactor comprised a Technicon research cartridge (oil bath) controlled at a temperature of 95° C. while the detector comprised a Technicon single channel colorimeter with a 570 nm optical interference filter and a 2.0 mm.×50 mm. flow cell. The sample injector comprised a Waters Intelligent Sample Processor. (WISP) The sample size was 1000 microliters.

The first and second mobile phase carrier comprised an aqueous solution of potassium phosphate, monobasic added at a flow rate of 0.6 ml/min. This solution was prepared by dissolving 160 ml. of methanol in 3.8 liters of deionized water. The solution was then adjusted to a pH of 2.3 with 85% phosphoric acid and normal HPLC degassing filtration procedures were followed. No additional mobile phase carrier was employed. The sample size employed was 1000 microliters.

A ninhydrin solution, a wetting reagent and argon were admixed with the eluent of the second chromatographic separation zone in an amount sufficient to prepare a glyphosate derivatized color complex, the concentration of which was indicative of the concentration of the glyphosate component in the eluent from the second chromatographic separation zone.

The ninhydrin solution was prepared by admixing 1100 ml. of dimethylsulfoxide, 800 ml. of deionized water, 400 ml. of 4-molar lithium acetate. Argon was bubbled therethrough for about 15 minutes where thereafter 32 grams of ninhydrin was added to the solution with stirring. In a separate beaker, 1.6 grams of solution was dissolved into two portions of 50 ml. dimethylsulfoxide with 5 ml. of previously prepared ninhydrin solution and was mixed together with argon bubbling. The argon was applied to the ninhydrin solution during the operation.

The wetting reagent was prepared by dissolving 10 ml. of Brij 35 surfactant and 800 ml. of deionized water with a few drops of concentrated sulfuric acid added to make an acid solution.

The peak height of the resulting glyphosate derivatized colored complex product was determined and compared with those obtained from previously prepared standards. The concentration of the colored complex in the reaction detector was related to the concentration of the glyphosate in the stock solution in order to obtain quantitative and qualitative information. The total run time per sample was 45 minutes.

EXAMPLE 2

An aqueous solution containing as a major component the isopropylamine salt of glyphosate and N-nitrosoamine as a component of interest at a trace level concentration was analyzed in accordance with the following procedure employing a chromatographic system similar to that shown the FIGURE.

A modified Griess post column reactor was employed as a detector comprising a single channel colorimeter. The sample size was 1000 microliters.

The first mobile phase carrier comprised an aqueous solution of 0.25 molar sodium chloride. The additional mobile phase carrier was admixed with the eluant of the first chromatographic separation zone and comprised water of grade equivalent to HPLC water while the mobile phase carrier associated with the second chromatographic separation zone comprised a solution of 0.043 molar ammonium phosphate and 20% methanol having a pH of 2.1. The second mobile phase carrier was prepared by admixing 20 grams of ammonium phosphate, 30 milliliters of 85% phosphoric acid, 3 liters of distilled water and adding 800 milliliters of methanol.

A modified Griess reactant solution was admixed with the eluent of the second chromatographic separation zone and comprised a solution of N-1-naphthalene ethylene diamine dihydrochloride and hydrobromic acid mixed reagent, a solution of sulfanilamide-HCl-Brij mixed reagent.

The first chromatographic separation zone comprised a chromatographic column having as packing therein anion ion exchange resin chloride form having a particle size in the range from about 45 to 180 microns, the second chromatographic separation zone comprised a chromatographic column having as packing therein anion ion exchange resin of phosphate form having a particle size in the range from about 8 to 12 microns.

The N-1-naphthalene ethylenediamine dihydrochloride/hydrogen bromide mixed reagent was prepared by adding 4.34 grams of N-1-naphthalene ethylenediamine dihydrochloride to 500 milliliters of distilled water in a 1-liter volumetric flask. The solution was stirred and 1 pint of 48% hydrobromic acid was added and the volume was adjusted accordingly to 1 liter was distilled water. The sulfanilamide-HCl-Brij 35 surfactant mixed reagent is prepared by dissolving 30 grams of sulfanilamide in 2600 milliliters of distilled water having 100 milliliters of Brij 35 and 300 milliliters of concentrated HCl. A Griess reactor was employed as the reaction detector system.

The flow rate of the first mobile phase was 2 milliliters per minute. The flow rate of the second mobile phase was 4 milliliters per minute.

The eluent of the first chromatographic separation zone was admixed with the aforedescribed additional mobile phase carrier comprising water in the ratio of 2:1 parts water to 1 part eluent to form a diluted eluent. The diluted eluent was then passed into an interstage storage zone for a time of about 5 minutes corresponding to the elution of compounds not of interest in applicants' multi-component composition from the first chromatographic column. After 5 minutes, the diluted eluent of the first chromatographic separation zone was passed to said second chromatographic separation zone. At the end of two minutes thereafter, the diluted eluent was then passed back to intermediate storage and thereafter a second mobile phase carrier comprising 0.043 M NH$_4$H$_2$PO$_4$, 20% methanol having a pH of 2.1 was passed to the second chromatographic separation zone.

The methanol solution was prepared by dissolving 20 grams NH$_4$H$_2$PO$_4$ 30 ml of 85% H$_3$PO$_4$ in 3 liters of distilled water and admixing therewith 800 milliters of methanol. The composition was cooled to 25° C.

The aforedescribed modified Griess solution was admixed with the eluant of the second chromatographic separation zone and was thereafter passed to a modified Griess reaction detector system wherein the concentration of n-nitrosoamine derivative was colorimetrically determined. The concentration of N-nitrosoamine was determined from the concentration of the N-nitrosoamine derivative. The total run time was 45 minutes.

What is claimed is:

1. A method of increasing the capacity of a chromatographic system useful for the quantitative determination of at least one component of interest in a multi-component composition at trace level concentration, said method comprising:

(a) admixing a portion of said multi-component composition with a first mobile phase carrier to form a chromatographically separable composition;
   (b) passing said chromatographically separable composition into a first chromatographic separation zone having packing therein thereby forming an eluent of each component of said multi-component composition;
   (c) retaining in said chromatographic separation system only the eluent of said component of interest;
   (d) admixing at least one additional mobile phase carrier with said retained eluent of said first chromatographic separation zone to form a diluted retained eluent;
   (e) passing said retained diluted eluent into a second chromatographic separation zone serially connected to said first chromatographic separation zone having packing therein;
   (f) passing a second mobile phase carrier into said second chromatographic separation zone thereby forming a purified eluent containing said component of interest in a concentrated form;
   (g) passing said purified eluent into an analytical detection system whereby the concentration of said component of interest is determined.

2. The method of claims 1 wherein said trace level is a concentration in the range from about 1 to about 1000 parts per billion by weight.

3. The method of claim 2 wherein said trace level is a concentration in the range from about 5 to about 100 parts per billion by weight.

4. The method of claim 3 wherein said portion of said multi-component composition is a sample size in the range from about 0.01 to about 5 milliliters.

5. The method of claim 4 wherein said sample size is in the range from about 1 to about 2 milliliters.

6. The method of claim 1 wherein said packing is ion exchange resin selected from the group consisting of polystyrene-divinyl benzene based resin and silica based chemical bonded packing material.

7. The method of claim 6 wherein said first and said second chromatographic separation zones comprise columns.

8. The method of claim 7 wherein said chromatographic separation zones comprise metallic columns.

9. The method of claim 1 wherein said multi-component aqueous solution is an aqueous solution of glyphosate.

10. The method of claim 1 wherein said multi-component composition comprises an aqueous solution of N-nitrosoamines.

11. A process of claim 10 wherein said packing employed in said first chromatographic separation zone is an anion ion exchange resin.

12. A process of claim 11 wherein said anion exchange resin comprises a chloride ion exchange resin.

13. The method of claim 12 wherein said packing employed in said second chromatographic separation zone is a silica based anion ion exchange packing material.

14. The method of claim 13 wherein said first mobile phase carrier comprises an aqueous solution of sodium chloride.

15. The method of claim 14 wherein said additional mobile phase carrier comprises water.

16. The method of claim 15 wherein said second mobile phase carrier comprises an aqueous solution of KH$_2$PO$_4$.

17. The process of claim 10 wherein said N-nitrosoamines comprises a polar substituted alkyl nitrosoamine.

* * * * *

UNITED STATES PATENT AND TRADEMARK OFFICE
CERTIFICATE OF CORRECTION

PATENT NO. : 4,454,043

DATED : June 12, 1984

INVENTOR(S) : Chihyuan C. Ting, David F. Tomkins, Melvin L. Rueppel

It is certified that error appears in the above-identified patent and that said Letters Patent is hereby corrected as shown below:

Column 1, line 9: "race" should be --trace--

Column 1, line 44: "antifacts" should be --artifacts--

Column 6, line 6: "applicants's" should be --applicants'--

Column 6, line 44: "wherein R" should be --where R--

Column 7, line 67: "methaol-" should be --methanol- --

Column 11, line 26: "was" should be --with--

Signed and Sealed this

Eleventh Day of December 1984

[SEAL]

Attest:

GERALD J. MOSSINGHOFF

Attesting Officer     Commissioner of Patents and Trademarks